(12) United States Patent
Hu

(10) Patent No.: US 10,939,988 B2
(45) Date of Patent: Mar. 9, 2021

(54) BALL-TYPE ANTI-REFLUX BILIARY STENT

(71) Applicant: Bing Hu, Shanghai (CN)

(72) Inventor: Bing Hu, Shanghai (CN)

( * ) Notice: Subject to any disclaimer, the term of this patent is extended or adjusted under 35 U.S.C. 154(b) by 0 days.

(21) Appl. No.: 16/439,456

(22) Filed: Jun. 12, 2019

(65) Prior Publication Data
US 2020/0129284 A1 Apr. 30, 2020

(30) Foreign Application Priority Data
Oct. 31, 2018 (CN) .......................... 201811285857.7

(51) Int. Cl.
*A61F 2/04* (2013.01)
*A61F 2/90* (2013.01)

(52) U.S. Cl.
CPC .................. *A61F 2/04* (2013.01); *A61F 2/90* (2013.01); *A61F 2002/041* (2013.01); *A61F 2230/0006* (2013.01); *A61F 2230/0069* (2013.01); *A61F 2250/0039* (2013.01)

(58) Field of Classification Search
CPC .............. A61F 2/915; A61F 2002/9155; A61F 2220/0025
USPC ..................................... 623/1.16–1.48, 23.68
See application file for complete search history.

(56) References Cited

U.S. PATENT DOCUMENTS

| | | | | |
|---|---|---|---|---|
| 2004/0167616 A1* | 8/2004 | Camrud | ..................... | A61F 2/86 623/1.16 |
| 2007/0179590 A1* | 8/2007 | Lu | ............................. | A61F 2/91 623/1.16 |
| 2013/0150950 A1* | 6/2013 | Schlick | ..................... | A61F 2/04 623/1.16 |
| 2014/0018935 A1* | 1/2014 | Wang | ..................... | A61F 2/2409 623/23.68 |
| 2016/0045342 A1* | 2/2016 | Yan | ......................... | A61L 31/16 623/1.16 |
| 2017/0042709 A1* | 2/2017 | Supper | ...................... | A61F 2/89 |
| 2017/0071766 A1* | 3/2017 | During | ...................... | A61F 2/90 |
| 2018/0361129 A1* | 12/2018 | Renner | ................. | A61M 29/02 |
| 2019/0142570 A1* | 5/2019 | Clerc | ............... | A61B 17/12022 604/9 |
| 2020/0170818 A1* | 6/2020 | Ganz | ..................... | A61F 5/0089 |

FOREIGN PATENT DOCUMENTS

| | | |
|---|---|---|
| CN | 201719412 U | 1/2011 |
| CN | 107510517 A | 12/2017 |
| CN | 108451678 A | 8/2018 |
| CN | 208371966 U | 1/2019 |

* cited by examiner

*Primary Examiner* — Suzette J Gherbi

(57) ABSTRACT

A ball-type anti-reflux biliary stent, including a meshed body, a cup and a ball. The cup and the ball are respectively provided at two ends of the meshed body. Inner diameters of the cup and the ball is larger than that of the meshed body. The meshed body includes a plurality of sections, and two adjacent sections are connected by a flexible wire. The cup of the stent is a cylinder open outwards, and the opening of the ball is connected to a tube having a substantially elliptical cross section. Therefore, a displacement of the stent is prevented for an accurate fixation of the stent. Moreover, the intestinal juice is prevented from flowing back into the biliary tract, avoiding infectious diseases.

4 Claims, 4 Drawing Sheets

BALL-TYPE ANTI-REFLUX BILIARY STENT

CROSS-REFERENCE TO RELATED APPLICATIONS

This application claims the benefit of priority from Chinese Patent Application No. 201811285857.7, filed on Oct. 31, 2018. The content of the aforementioned application, including any intervening amendments thereto, is incorporated herein with reference in its entirety.

TECHNICAL FIELD

The present disclosure relates to stents implanted in human bodies, and more particularly to a recyclable anti-reflux biliary stent.

BACKGROUND OF THE INVENTION

Lumens in the human body lead to diseases such as stenosis or obstruction due to various causes and lesions. The commonly used method to treat such diseases is to implant a metal stent into stenosis and obstruction sites to ensure the patency of the lumen.

The existing stents comprise bare-metal stents and covered stents. The film coating process of the covered stent is to immerse the whole stent into polymer liquid for casting film in a wall-hanging manner; or to attach the polymer membrane materials to surfaces of the stent and to heat the whole stent allowing attachment of the membrane onto the surfaces of the stent. The stent is prone to displacement due to its poor compliance performance, and an anti-reflux function for food or body fluid is not available.

Therefore, there is a need for an ultra-flexible, anti-displacement, anti-reflux and recyclable biliary stent in clinic, which can adapt to the physiology structures of biliary tract in the human body, and prevents food from flowing back to the biliary tract.

SUMMARY OF THE INVENTION

To solve the technical problem in the prior art, the present disclosure provides a ball-type anti-reflux biliary stent that is recyclable and is adaptable to the physiology structure of the human biliary tract.

The present invention provides a ball-type anti-reflux biliary stent, comprising a meshed body, a cup and a ball. The cup and the ball are respectively provided at two ends of the meshed body. Inner diameters of the cup and the ball are larger than that of the meshed body. The meshed body comprises a plurality of sections, and two adjacent sections are connected by a flexible wire.

The opening of the ball is connected to a tube having a substantially elliptical cross section. A ratio of a length of the tube to a diameter of the ball is 2:3 to 3:2, and a length-to-width ratio of the tube is 2:1 to 6:1.

The cup is a cylinder open outwards. A joint surface between the meshed body and the cup is a curved surface, which reduces a resistance for liquids flowing from the cup.

In some embodiments, the flexible wire connecting the two adjacent sections has a length of 2-6 mm.

In some embodiments, the meshed body, the cup and the ball are formed of braided nickel-titanium wires, which facilitates supporting the shape of the stent, so that bile can normally flow out from the stent while maintaining a good anti-reflux effect.

In some embodiments, outer surfaces of the meshed body, the cup and the ball are covered with a silica gel membrane, which can prevent tissue hyperplasia from growing into the stent, ensuring that the stent can be successfully recycled.

The present disclosure has the following advantages.

1. The meshed body includes a plurality of sections connected by the flexible wire, so that the stent can be easily bent at a certain angle to adapt to the physiological anatomy structure of the biliary tract. In this way, the stent has an improved compliance over the existing stent having an integrated structure of the stent and the film.

2. The stent is designed to have a cup formed as a cylinder open outwards, and a ball with an opening connected to a tube having a substantially elliptical cross section. Therefore, on one hand, the displacement of the stent is prevented for an accurate fixation of the stent, and on the other hand, the intestinal juice is prevented from flowing back into the biliary tract, avoiding infectious diseases.

BRIEF DESCRIPTION OF THE DRAWINGS

The present invention will be further described in detail below with reference to the accompanying drawings and embodiments, from which the advantages of the above and/or other aspects will be more apparent.

DETAILED DESCRIPTION OF EMBODIMENTS

Figure 1:
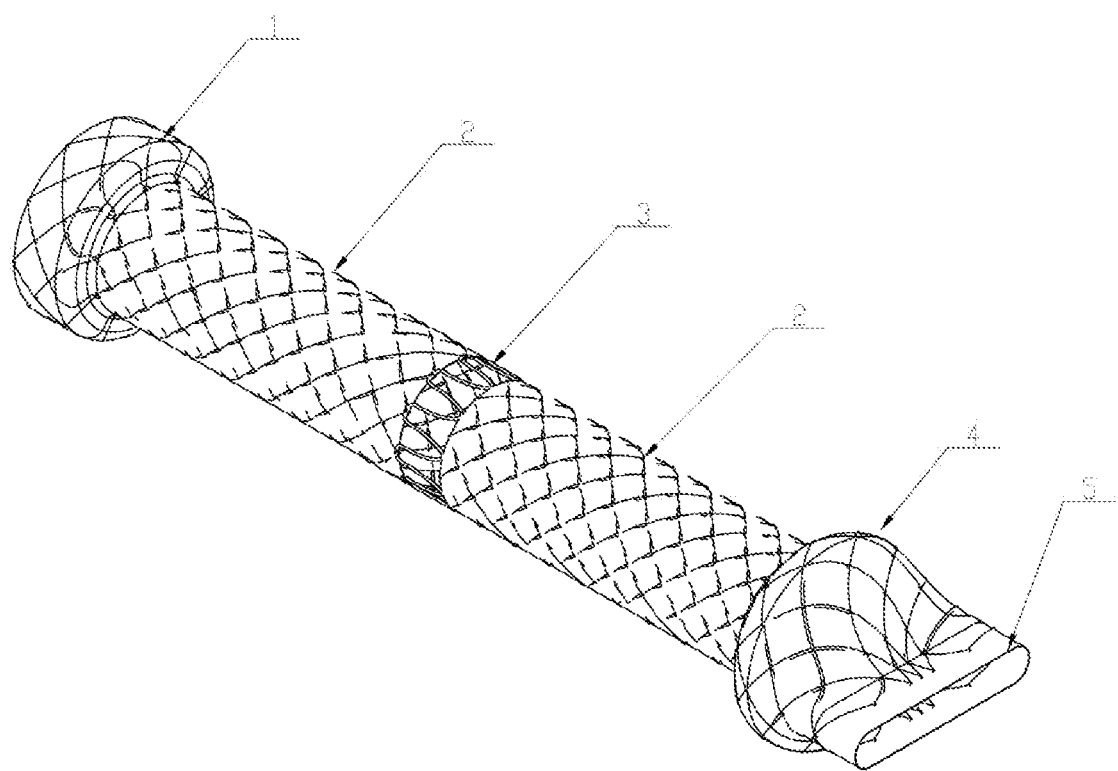
FIG. 1 is a perspective view of an anti-reflux biliary stent.

The present disclosure can be better understood according to the following embodiments.

Structures, proportions, sizes shown in the drawings are only illustrative of the disclosure in the specification for understanding and reading by those skilled in the art, and are not intended to limit the conditions at that the present invention is implemented. Any modifications of structures, changes in proportions or adjustments of sizes, which do not affect the achievable effects and purposes, shall fall within the scope of the present disclosure. As used herein, terms such as "upper", "lower", "front", "rear", "middle" are also used for illustrative purposes, and are not intended to limit the scope of the present disclosure. Any changes or adjustments of the relative relationship without departing from the substantial technical contents are considered to be within the scope of the present disclosure.

Figure 2:
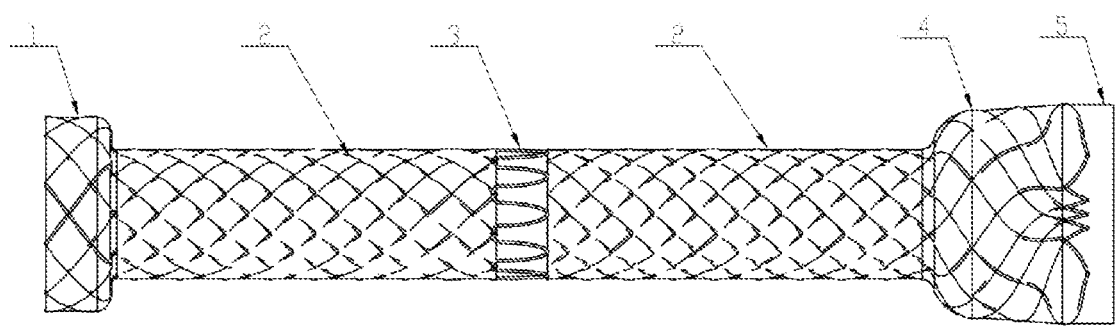
FIG. 2 is a top view of the anti-reflux biliary stent.
Figure 3:
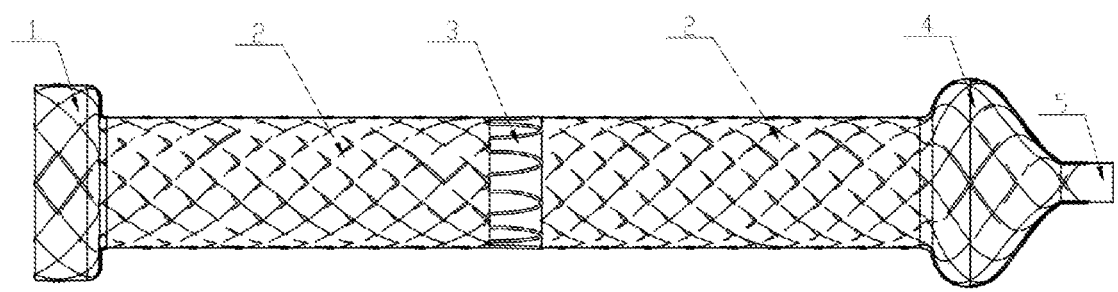
FIG. 3 is a side view of the anti-reflux biliary stent.
Figure 4:
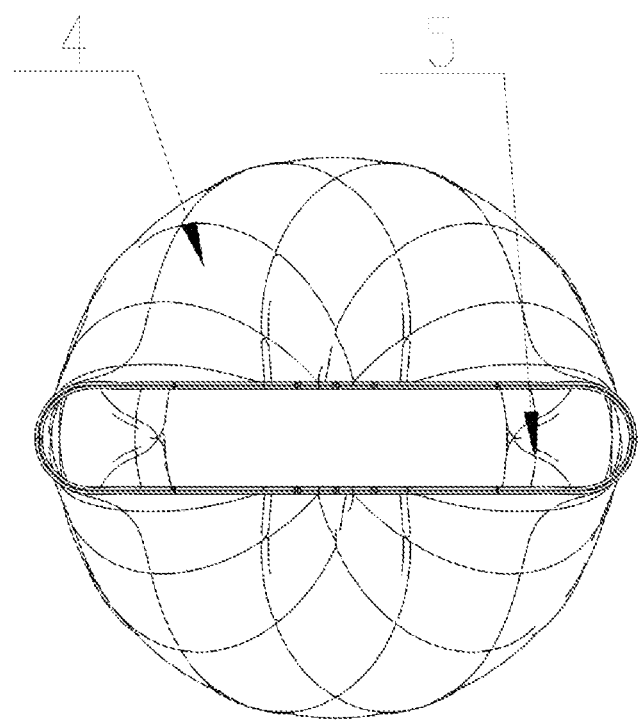
FIG. 4 is a partial enlarged view showing a ball of the anti-reflux biliary stent.

As shown in FIGS. 1 and 2, an anti-reflux stent includes a meshed body 2, a cup 1 and a ball 4. The cup 1 and the ball 4 are respectively provided at two ends of the meshed body 2. Inner diameters of the cup 1 and the ball 4 are larger than that of the meshed body 2, which can prevent a displacement of the stent for an accurate fixation of the stent. The cup 1 is a cylinder open outwards. A joint surface between the meshed body 2 and the cup 1 is a curved surface. The opening of the ball 4 is connected to a tube 5 having a substantially elliptical cross section. A ratio of a length of the tube 5 to a diameter of the ball 4 is 1:1. A length-to-width ratio of the tube 5 is 5:1. In this way, the intestinal juice can easily flow from the cup 1, and flow out of the ball 4. However, a reverse inflow from the tube 5 is hard to achieve, so that the intestinal juice is prevented from flowing back into the biliary tract, avoiding infectious diseases.

The meshed body 2, the cup 1 and the ball 4 are formed of braided nickel-titanium wires, and outer surfaces of the meshed body, the cup and the ball are covered with a silica gel membrane, which is beneficial for the shape holding of the stent and prevents tissue hyperplasia from growing into the stent enabling a recycle of the stent.

The meshed body 2 includes two sections which are connected by a flexible wire 3 having a length of 3 cm in the middle, so that the stent can be easily bent at a certain angle to adapt to the physiological anatomy structure of the biliary tract. In this way, the stent has an improved compliance over the existing stent having an integrated structure of the stent and the film.

The present disclosure provides a concept and a spirit for the ball-type anti-reflux biliary stent, and various implementations can be used to implement the present invention. The above-mentioned is only some preferred embodiments. It should be noted that any improvements and modifications may be made by those skilled in the art without departing from the principle of the disclosure, and shall fall within the scope of the present disclosure. The unspecified components in the embodiments can be implemented by using existing techniques.

What is claimed is:

1. A ball-type anti-reflux biliary stent, comprising:
   a meshed body,
   a cup, and
   a ball with an opening;
   wherein the cup and the ball are respectively provided at two ends of the meshed body; inner diameters of the cup and the ball are larger than that of the meshed body; the meshed body comprises a plurality of sections, and two adjacent sections are connected by a flexible wire;
   the opening of the ball is connected to a tube having a substantially elliptical cross section; a ratio of a length of the tube to a diameter of the ball is 2:3 to 3:2; and a length-to-width ratio of the tube is 2:1 to 6:1; and
   outer surfaces of the meshed body, the cup and the ball are covered with a silica gel membrane.

2. The ball-type anti-reflux biliary stent of claim 1, wherein the cup is a cylinder open outwards; and a joint surface between the meshed body and the cup is a curved surface.

3. The ball-type anti-reflux biliary stent of claim 1, wherein the flexible wire connecting the two adjacent sections has a length of 2-6 mm.

4. The ball-type anti-reflux biliary stent of claim 1, wherein the meshed body, the cup and the ball are formed of braided nickel-titanium wires.

* * * * *